United States Patent [19]

Barnum et al.

[11] Patent Number: 5,449,801
[45] Date of Patent: Sep. 12, 1995

[54] REACTIVE DISTILLATION PROCESS FOR FREE RADICAL HALOGENATION

[75] Inventors: Chris S. Barnum, Newark; Charles T. Blaisdell, Middletown, both of Del.

[73] Assignee: E. I. Du Pont de Nemours and Company, Wilmington, Del.

[21] Appl. No.: 91,507

[22] Filed: Jul. 14, 1993

[51] Int. Cl.⁶ .............................................. C07F 7/08
[52] U.S. Cl. .................................... 556/436; 556/476; 556/477; 204/157.64; 204/157.63; 204/157.74; 204/157.87; 204/158.12; 568/56; 568/388; 568/393; 570/185; 570/252; 570/255
[58] Field of Search ............ 204/157.64, 157.63, 204/157.74, 157.87, 158.12; 556/477, 436, 476; 568/56, 388, 393; 570/252, 255, 185

[56] References Cited

U.S. PATENT DOCUMENTS

| | | | |
|---|---|---|---|
| 2,510,149 | 6/1950 | Speier, Jr. | 260/448.2 |
| 2,715,134 | 8/1955 | Speier, Jr. | 260/448.2 |
| 3,840,447 | 10/1974 | Lucking et al. | 204/157.74 X |
| 3,844,915 | 10/1974 | Takamizawa et al. | 204/157.64 X |
| 3,912,604 | 10/1975 | Lucking et al. | 204/158 |
| 4,101,397 | 7/1978 | Kotzsch et al. | 204/158 HA |
| 4,659,852 | 4/1987 | Shinohara et al. | 556/488 X |
| 4,874,488 | 10/1989 | Crabtree et al. | 204/157.74 X |

FOREIGN PATENT DOCUMENTS 60-064702 4/1985 Japan .

Primary Examiner—Paul F. Shaver

[57] ABSTRACT

A process for the selective high yield halogenation $R-CH_3$ wherein R is

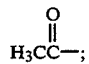

$Si(Cl)_m(CH_3)_n$, wherein m is 1 to 3, n is 1 to 3 and m+n is 3; phenyl; or phenyl substituted with Cl, Br, F, $OR^1$, $SR^1$ or $NO_2$; $R^1$ is $C_1$–$C_3$ alkyl; and X is chlorine or bromine; under reactive distillation conditions which continuously and selectively separate the mono, di, or trihalogenated product from the reaction zone and which does not require recycling of the starting materials is disclosed.

20 Claims, 2 Drawing Sheets

REACTIVE DISTILLATION PROCESS FOR FREE RADICAL HALOGENATION

FIELD OF THE INVENTION

The present invention relates to a process for the selective, high yield halogenation of particular silyl, phenyl, or carbonyl compounds under reactive distillation conditions which doesn't require recycling of the starting material.

BACKGROUND OF THE INVENTION

Free radical halogenation is a well known reaction that is often carried out under a variety of conditions. The use of light, heat or microwaves have been used to generate reactive halogen radicals which quickly react with a variety of organic compounds to yield halogenated derivatives. However, it is the reactivity of the halogen radicals which cause problems with selectivity. Often, in addition to the desired monohalogenated derivative, higher polyhalogenated derivatives are formed. This problem is generally dealt with by running the reaction only to low conversion and then separating the unreacted starting material and recycling it. By conducting the reaction only to low conversion, the ratio of monohalogenated product to starting material remains high thereby reducing the formation of higher halogenated products. The disadvantage to this process is that it requires a considerable investment in equipment to effect the recycling, and low productivity per unit investment.

A typical low conversion halogenation process of the prior art employs recycling of the starting material to achieve high yields of monohalogenated product, while minimizing the yields of undesirable polyhalogenated products. Typically in this process, the halogen feed is directed into the liquid substrate contained in the reaction pot. The reaction pot is heated and simultaneously irradiated with light to promote the formation of halogen radicals which subsequently react with the organic substrate. The low conversion is accomplished by introducing only a fraction of the halogen necessary to complete the reaction. This avoids polyhalogenation since as the reaction proceeds, product is formed which remains in the reaction pot and is thus available for reaction with the halogen radicals to form polyhalogenated derivatives. The unreacted starting material is separated from the monohalogenated product (typically only 5-10% of the mixture) and recycled. Larger amounts of halogen can be introduced to yield higher percentages of monohalogenated product only at the expense of increasing amounts of polyhalogenated derivatives which cannot easily be recycled.

U.S. Pat. Nos. 2,510,149 and 2,715,134 both disclose the chlorination of organosilicon derivatives in the vapor or liquid phase. These procedures however do not allow the efficient, continuous separation of product and starting material necessary for high conversion to product while minimizing yields of polyhalogenated by-products. U.S. Pat. No. 4,101,397 discloses a low conversion process for the halogenation of organosilanes which employs continual recycling of the unreacted organosilane to provide high yields. The feed rate of the reactants is used to control the reaction temperature to avoid a potentially violent reaction or explosion. Thus a need exists for an improved efficient and selective process for monohalogenation. The present invention provides such a process for selective high yield halogenation of particular organic compounds without recycling of the starting material.

SUMMARY OF THE INVENTION

This invention comprises an improved selective free radical halogenation process. In a free radical halogenation process for the preparation of compounds of Formula I $$R\text{---}CY \qquad \qquad I$$

wherein Y is $H_2X$, $HX_2$ or $X_3$;

R is $H_3CC\text{---}$, $\text{---}Si(Cl)_m(CH_3)_n$ wherein $m=0$ to 3, $n=0$ to 3, and $m+n=3$; or phenyl optionally substituted with Cl, Br, F, $OR^1$, $SR^1$ or $NO_2$; $R^1$ is $C_1$-$C_3$ alkyl; and X is Cl or Br; by reacting R---$CH_3$ and $X_2$ wherein R and X are as defined for Formula I, the improvement comprises conducting the reaction in a designated reaction zone beneath a condenser zone and above a separation zone affixed to a reaction pot with the separation zone continuously and selectively separating the desired halogenated product of Formula $RCH_2X$, $RCHX_2$ or $RCX_3$ from the reaction zone. Preferably the process is used for selective monohalogenation.

DETAILED DESCRIPTION OF THE INVENTION

The present invention comprises use of a distillative separation process to create a reaction zone with a high concentration of starting substrate relative to halogen and which separates out the desired halogenated product as it is formed, and conducting the halogenation in that zone. Compounds of Formula II, R---$CH_3$, are reacted with halogen $X_2$, wherein R and X are as defined above in Formula I to generate the desired halogenated product of Formula IA according to Equation 1. Product of Formula IA can be further halogenated to generate product of Formula IB, which can also be further halogented to generate product of Formula IC according to Equations 2 and 3 respectively. A high ratio of reactant II, IA or IB to $X_2$ is maintained in the reaction zone by controlling the feed rate of $X_2$ and reaction pot temperature. Since the reaction zone contains both liquid and vapor and the reaction can take place in either, the effective ratio of reactant to $X_2$ is higher than the ratio of reactant boiling up to $X_2$. This results in a high ratio of starting material to product, further aided by the distillative process which continually removes the desired product based upon the temperature maintained in the separation zone. This process can be run either as a batch or in a continuous mode and proceeds according to the following Equations 1 to 3.

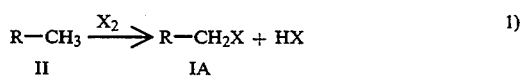

-continued $$R-CH_2X \xrightarrow{X_2} RCHX_2 + HX \quad\quad 2)$$
$$\text{IA} \quad\quad\quad \text{IB}$$

$$R-CHX_2 \xrightarrow{X_2} RCX_3 + HX \quad\quad 3)$$
$$\text{IB} \quad\quad\quad \text{IC}$$

The products IA, IB, and IC are each subsets of Formula I, RCY, wherein Y is $HX_2$, $H_2X$, or $X_3$. Future references to Formula I includes these subsets wherein R and X are as defined above.

Figure 1:
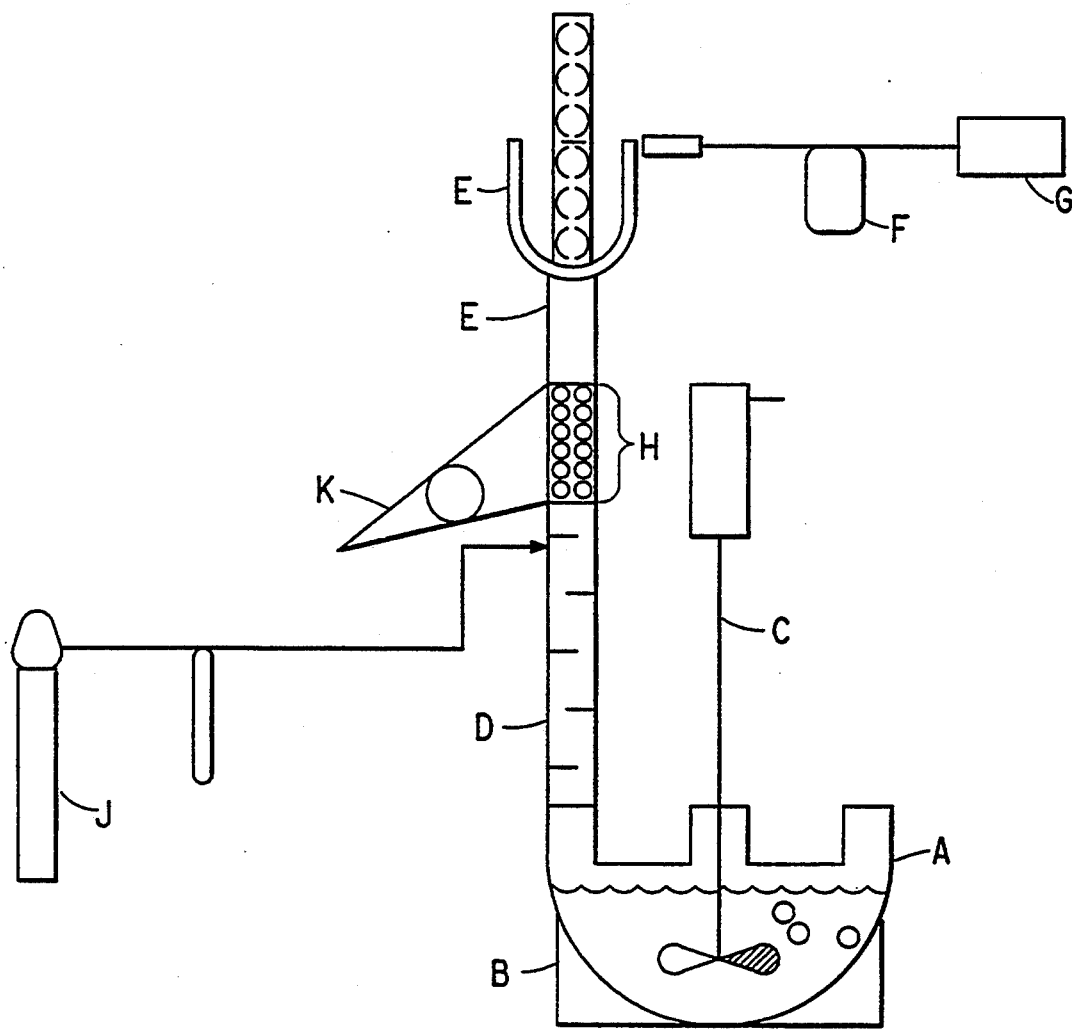
FIG. 1 depicts the process of the present invention operated in a batch mode.
Figure 2:
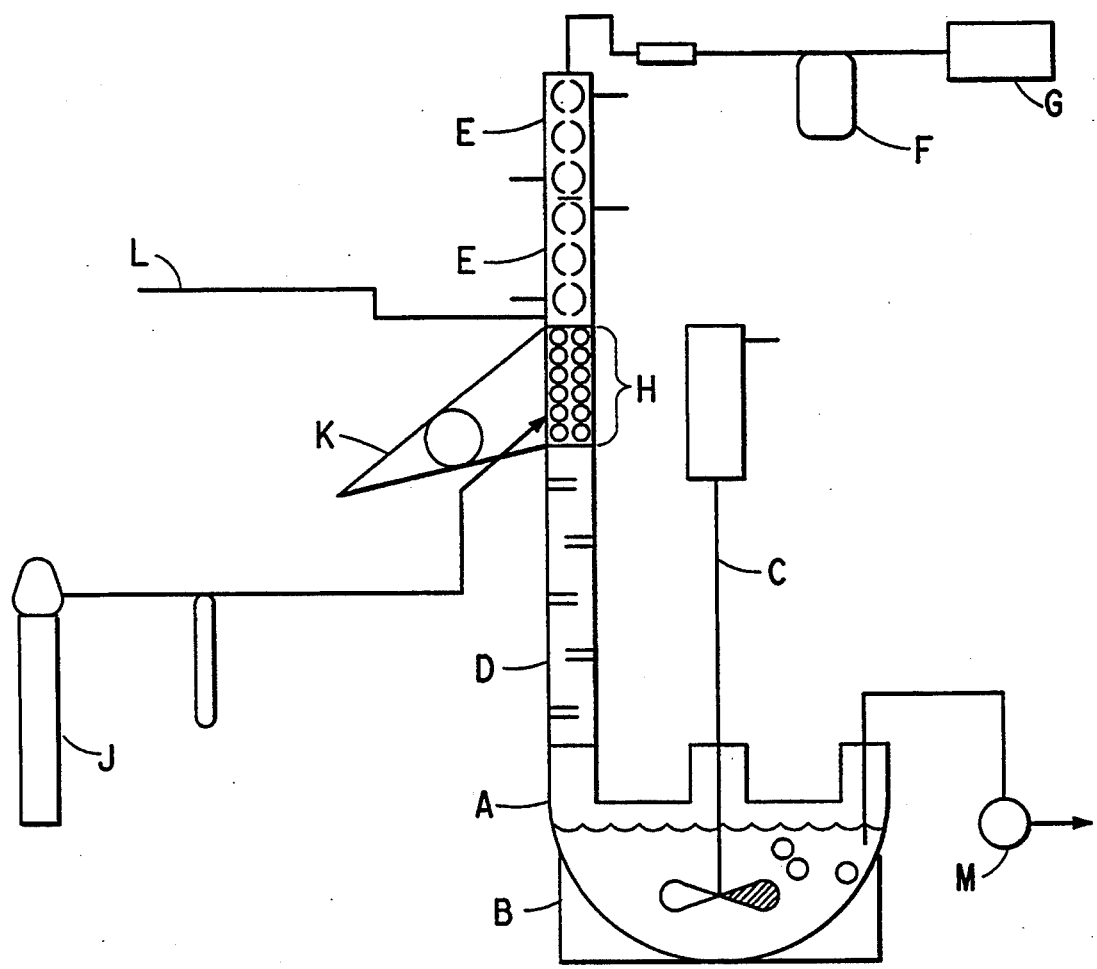
FIG. 2 depicts the process of the present invention operated in a continuous mode.

In the process of the present invention, halogen is introduced not into the reaction pot as is done in a conventional low conversion process but instead, into the designated reaction zone H as illustrated in FIG. 1. The reaction zone is situated such that there is a high concentration of starting material (present as both vapor and liquid condensate). As $X_2$ is introduced, it intimately mixes with rising vapor consisting mainly of $R-CH_3$, and enters the reaction zone where either by heat, a free radical-generating chemical agent, or irradiation from a light or microwave source, it is converted to its free radical. The generated halogen radicals undergo reaction with compounds of Formula II according to Equation 1 in the liquid and vapor phase. When operating the process in a batch mode as depicted in FIG. 1, the halogen is preferably introduced at or near the bottom of the reaction zone, and the halogen feed is stopped when the separation column temperature rises to the boiling point of the desired halogenated product. When operating the process in a continuous mode as depicted in FIG. 2, the halogen is preferably introduced at or near the bottom of the reaction zone, and the separation column temperature profile is maintained by controlling the addition rate of halogen or reactant to achieve the boiling point of reactant on the top trays and the boiling point of halogenated product IA, IB or IC on the bottom trays. The process of the present invention is especially preferred for preparation of monohalogenated product IA. As the monohalogenated product of Formula IA is formed, it is removed from the reaction zone by virtue of its higher boiling point. Selectivity is achieved by maintaining high a $R-CH_3/X_2$ ratio in the reaction zone through an appropriate feed rate of $X_2$. Since the higher boiling product IA is continuously removed via the distillative process, the concentration of IA is low thereby reducing the formation of higher polyhalogenated derivatives. If it is desired to generate a greater amount of polyhalogenated derivatives IB or IC, a low ratio of reactant (IA or IB) to $X_2$ can be maintained through control of the $X_2$ feed rate, and appropriate temperature maintenance in the separation (distillation) zone. The appropriate temperature in the lower half of the separation zone is the boiling point of the desired product.

The increased selectivity observed for the free radical halogenation of the present invention results in higher conversions to product without the need for recycling the starting material and the equipment necessary for recycling. Furthermore, higher conversions and greater selectivity yield products of higher purity.

FIG. 1 illustrates a batch process of the present invention wherein the starting material of Formula II is charged to the reaction pot A subjected to heat by heating means B. Reaction pot A is equipped with a stirrer C and a separation zone D, preferably in the form of a distillation column. The distillation column D is equipped with a condenser E which is further connected to low-temperature trap F and scrubbing system G. Between the distillation column and below the condenser is a reaction zone H. The reaction zone is subject to heat, light or irradiation from source K. The reaction zone is designed as an area wherein a high concentration of starting material is present both in the vapor and liquid phases, a low concentration of product is maintained and wherein halogen free radicals are formed. Reaction zone H may be an integral part of the distillation column D or may alternatively be added atop the distillation column D between the column and the condenser E. The reaction zone is further designed to allow for the retention of starting material in the liquid form. This arrangement allows for the development of a zone where the concentration of reactant is maintained at a high level as a liquid and a vapor. Vaporized starting material enters the reaction zone from the bottom while liquid starting material enters from the top as a result of its condensation on the condenser. As the reaction pot is heated, the starting material begins to vaporize and move up the distilling column. The halogen $X_2$ is fed into the bottom of reaction zone H from source J. When the vapor reaches the $X_2$ feed zone, it intimately mixes with $X_2$. The resultant mixture of starting materials enters the reaction zone wherein $X_2$ is converted to its free radical form by a source K of light, heat or irradiation, and reacts with the starting material of Formula II according to Equation 1. As the halogenated product is formed, it is removed from the reaction zone by virtue of its higher boiling point and returns to the reaction pot thereby minimizing, at any one time, the concentration of product in the reaction zone. Preferably the monohalogenated product IA is removed from the reaction zone to minimize the formation of polyhalogenated products. The starting organic substrate, $R-CH_3$, which makes it's way out of the reaction zone through the top, condenses and is returned to the reaction zone in the form of a liquid. The monohalogenated product that returns to the reaction pot is kept from reentering the reaction zone by the distillative separation process afforded by the use of a separation zone in the form of a distilling column. Organics which move beyond the condenser are condensed in a cold trap F. The scrubbing system G removes the HX by-product. If the dihalogenated or trihalogenated product is desired the distillation column is maintained at the appropriate temperature so that the desired product is returned to the reaction pot and doesn't enter the reaction zone.

In principle, situating the $X_2$ feed anywhere between the condenser and above the refluxing reaction pot will provide an increase in product selectivity over a conventional low-conversion batch process. By placing the $X_2$ feed above the liquid level in the reaction pot, the concentration of product (present in the vapor form) is always lower than that present as a liquid in the pot. As such, increased selectivity is observed in the reduced formation of the undesired halogenated derivatives. In practice, locating the $X_2$ feed beyond the distillative separation afforded by the separation zone (distillation column) maximizes the observed selectivity. The purpose of the distillation column is to separate the desired halogenated product, preferably the monohalogenated product, from the starting material. Since the boiling point of the product is higher, the ratio of starting material to product increases up the column. As such, locating the $X_2$ feed at the top of the distillation column, just below the reaction zone, ensures the highest reactant/product ratio and thereby ensures minimum formation of the undesired halogenated derivatives. The $X_2$ feed can be directly into the reaction zone or even above it. However, to ensure complete mixing, locating the feed just below the reaction zone is preferred. The rate of $X_2$ feed, or $R-CH_3$ feed in continuous operation, should be adjusted so that the reflux ratio, defined as the concentration of $II/X_2$ in the reaction zone, is greater than or equal to 4/1, preferably 7/1, most preferably 10/1 or higher. Lower ratios result in less selectivity with higher concentrations of polyhalogenated derivatives. To produce the dihalogenated product, a ratio of $RCH_2X$ (reactant as defined in equation 2) to $X_2$ of greater than or equal to 4/1, preferably 7/1 and most preferably 10/1 or higher is maintained in the reaction zone. Further, the feed rate is monitored so that the temperature of reaction zone does not exceed 6° C. higher, preferably does not exceed 3° C. higher, than the boiling point of the reactant ($RCH_2X$). In general, for optimizing yield of the monohalogenated product, the temperature of the reaction zone should be maintained at less than or equal to about 6° C. or higher, preferably less than or equal to about 3° C. higher than the boiling point of the starting material $RCH_3$. As the temperature of the reaction zone increases significantly above the temperature of the boiling point of $RCH_3$, high concentrations of IA enter the reaction zone from the distillation column and thus higher yields of polyhalogenated derivatives IB and IC are observed. To optimize yield of the dihalogenated product IB, the feed rate is monitored so that the temperature of the reaction zone does not exceed 6° C. higher, preferably does not exceed 3° C. higher, than the boiling point of $RCH_2X$. To optimize the yield of the trihalogenated product IC, the reaction zone temperature should be at or above the boiling point of $RCHX_2$.

In theory, the reaction zone can be located anywhere between the reaction pot and the condenser. The reaction zone for a conventional low-conversion batch halogenation is the reaction pot itself. In the present invention it has been found advantageous to locate the reaction zone above the reaction pot, preferably above the separation zone (distillation column). Such an arrangement allows taking full advantage of the distillative separation of product and reactant afforded by the distilling column. This separation maximizes the reactant/product ratio entering the reaction zone. The reaction zone is further defined as that region where $X_2$ is promoted to form its free radical as shown below in Equation 4.

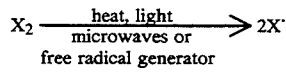

4)

The reaction zone can be an integral part of the separation column, usually located at the top of the column so as to ensure adequate separation of reactant and product in the lower part of the column. Alternatively, the reaction zone can be affixed atop the separation column. In either arrangement, the reaction zone is designed to maximize the concentration of reactant, both in the liquid and vapor phase. To achieve retention of the liquid, the reaction zone is preferably designed with a large surface area. For example, the zone can be packed with glass beads to hold-up the liquid which enters the reaction zone from the top after condensing at the condenser.

The energy source for free radical formation in the reaction zone is typically heat, microwave radiation or light. Light is normally preferred for ease of use and availability. The light source is any source which emits light of a suitable wavelength to form halogen radicals according to Equation 4. A preferred wavelength is between 300–400 nm.

The choice of distillation column is dependent upon the desired separation and the difference in the boiling points of the starting material and the product. The column is chosen so as to effect a minimal separation equivalent to five theoretical plates. Less efficient separation yields a lower reactant/product ratio entering the reaction zone which results in higher concentrations of polyhalogenated derivatives being formed. More efficient columns can be employed, however their use should be economically justified in terms of energy input, reaction time and desired selectivity. Any number of columns designed for fractional distillation can be used as known to one skilled in the art. Examples include but are not limited to simple distillation columns packed with glass beads or other suitable packing material, Vigreux and Oldershaux. The column can also be optionally insulated or heated.

Vent losses are trapped by a dry-ice trap or other cold trap. The by-product HX gas is treated in the manner most economically feasible, such as scrubbing with an appropriate scrubbing agent, or used as a by-product.

As the reaction proceeds, the reaction pot temperature increases. When the pot temperature and the lower part of the distillation column reach approximately the temperature of the boiling point of the desired halogenated product, the $X_2$ feed is stopped and the product separated from the reaction pot mixture by any number of conventional procedures such as fractional distillation. Although small amounts of starting material and polyhalogenated products will be present in crude material of the reaction pot, the purified yields of monohalogenated are typically 90% (based on II) or greater without the need to continually recycle starting material as is done in a conventional low-conversion process. Similar yields can be obtained for the di- and trihalogenated products.

The process is easily amenable to continuous operation. FIG. 2 illustrates a typical continuous process for the present invention. The letters A through J have the same designations as previously described for FIG. 1. The feed of substrate of Formula II is designated as L. A pump for the removal of product is designated as M. This process is similar to the batch process except that at equilibrium, starting material is fed into the system at such a rate as to maintain an equilibrium distillative separation of reactant and product within the distillation column and withdrawing product from the reaction pot at such a rate as to maintain a constant volume. In some instances, it is advantageous to use a larger distillation column in the continuous operation than needed for the batch operation. The position of the feed of the starting material in a continuous process is not critical as long as it is introduced into the system at a point which contains a high concentration of starting material. The starting material feed is conveniently located near the reaction zone, preferable above the reaction zone. The operating pressure of the system is dependent upon the nature of the starting materials and the products. For ease of operation ambient pressure is preferred, however, when the product is unstable or is high boiling the process of the present invention can be operated a reduced pressure. For the continuous process the feed rates of both $X_2$ and reactant can be adjusted to maintain the desired ratio of reactant/$X_2$.

The process of the present invention is useful in obtaining high yields of the monohalogenated product of Formula IA without investment in the equipment to effect recycling of the starting material. Such equipment and its maintenance are very costly. The monohalogenated silicon and phenyl compounds of Formula IA have known uses such as adhesives in resins and thermoplastics. The process of the present invention is also useful in obtaining high yields of the di- or trihalogenated products in a selective manner.

The following Examples further illustrate the invention, but are not intended to limit it in any manner.

EXAMPLE 1

PREPARATION OF DICHLORO(CHLOROMETHYL)METHYLSILANE BY REACTIVE DISTILLATION BATCH PROCESS

To the apparatus as illustrated in FIG. 1, configured with a 250 mL 4-neck round bottom flask and a 5 plate 1 inch Oldershaux column, 107.0 g of dichlorodimethylsilane was charged to the pot and brought to reflux. The reaction zone was then irradiated with light from a light source equipped with a 200 watt tungsten light bulb. Chlorine gas was then charged at a rate of 0.3 g/min. After 58.1 g of chlorine was added, the pot temperature had risen to 123° C. The chlorine feed was ceased, the light turned off and the reaction was allowed to cool to ambient temperature. The reaction pot contained 123.9 g of material whose composition by gas chromatography was determined (area %) as 4.3% dichlorodimethylsilane (DCDMS), 91.2% dichloro(chloromethyl)methylsilane (DCCMMS) and 1.2% overchlorinated products. Approximately 1.6 g of presumably similar material remained in the system with an additional 5.2 g of material recovered from the dry-ice trap. The composition of the material in the trap as determined by gas chromatography area % was 89.2% DCDMS, 9.6% DCCMMS and 1.2% polychlorinated products.

COMPARATIVE EXAMPLE A

PREPARATION OF DICHLORO(CHLOROMETHYL)METHYLSILANE BY A CONVENTIONAL BATCH PROCESS

To a 250 mL 4-neck round bottom flask equipped with a dry-ice condenser, stirrer, and inlet feed for chlorine gas, and surrounded by a heating mantle was charged 129.1 g of dichlorodimethylsilane. The system vented through a dry ice trap and scrubber system. While stirring, the reaction flask was brought to reflux and then irradiated with a 200 watt tungsten light source while 71 g of chlorine gas is bubbled directly into the pot through a dip tube at a rate of approximately 0.25 g/min. The flask temperature rose from 71° C. to 98° C. during this addition at which point the heat, chlorine feed and the light were discontinued. The resulting mixture consisted of 155.8 g of material which by gas chromatography area % showed 33.4% dichlorodimethylsilane, 43% dichloro(chloromethyl)methylsilane and 23.6% polychlorinated products.

EXAMPLE 2

PREPARATION OF DICHLORO(CHLOROMETHYL)METHYLSILANE BY REACTIVE DISTILLATION CONTINUOUS PROCESS

The apparatus employed was as illustrated in FIG. 2, configured with a 250 mL round 4-neck bottom flask as a reaction pot, a pump to remove product from the reaction pot, and a 15 plate 1 inch Oldershaux column. The reaction pot was charged with 119.9 g of dichlorodimethylsilane as in Example 1 and brought to a reflux. The reaction zone was irradiated with a 200 watt tungsten light after which chlorine was charged at of 0.3 g/min. When the pot temperature had risen to 122°–123° C., and the temperature of the fourth tray of the Oldershaux column had risen to 73°–74° C., a dichlorodimethylsilane feed was started at the top of the reaction zone at slightly more than a 1:1 ratio with the chlorine feed. The dichlorodimethylsilane feed was then adjusted to maintain the temperature at the 5th plate from the column bottom at approximately 80° C. and the pot temperature at approximately 123° C. When the temperature profile stabilized, the dichloro(chloromethyl)methylsilane product was removed from the pot via the pump at a rate to maintain a constant level. The crude product being withdrawn had a composition by gas chromatography area % as 94.6% of the titled product and 5.4% polychlorinated products. No starting material was detectable. The system can be operated under these conditions indefinitely, or shut down and restarted each day. To restart the system, the reaction pot was heated to achieve strong reflux with no flooding. After the temperatures had equilibrated in the column, either $Cl_2$ or dichlorodimethylsilane feed was started to achieve the temperature profile described above. If the temperatures were greater than the desired operating temperature, dichlorodimethylsilane was fed first. If the temperatures were less than the desired operating temperatures, $Cl_2$ was fed first. When the desired operating temperature was achieved, the other feed was started. and the system became capable of running indefinitely.

EXAMPLE 3

PREPARATION OF (BROMOMETHYL)BENZENE BY A REACTIVE DISTILLATION BATCH PROCESS

The apparatus employed was as illustrated in FIG. 1 except that the lower condenser was replaced with a reflux splitter. Toluene, 107.5 g, was charged to the reaction pot and brought to reflux. The reaction zone was then irradiated with 200 watt tungsten light and then system was charged with 169.9 g of bromine at a rate of approximately 0.25 g/min during which time the pot temperature reached 200° C. and the bromine feed was discontinued. After a short hold at this temperature, the irradiation was terminated and the reaction allowed to cool to ambient temperature. The flask contained 188.4 g of material whose composition by gas chromatography area % was 12.75% toluene, 82.8% (bromomethyl)benzene and 4.5% unidentified by-product. Approximately 2 grams of material of similar composition remained in the system.

EXAMPLES 4–7

The apparatus and procedure of Example 1 were employed to prepare chloro(chloromethyl)dimethyl silane, (chloromethyl)trimethyl silane, trichloro(- chloromethyl) silane, and chloroacetone by chlorination of trimethylchlorosilane, tetramethylsilane, methyl trichloride and acetone respectively. The initial and final reaction pot temperatures, yield, and gas chromatographical analysis of the product is summarized in Table 1.

TABLE 1

| Example | Reactant | Pot Temperature, °C. Initial | Pot Temperature, °C. Final | Yield | Product | |
|---|---|---|---|---|---|---|
| 4 | Cl—Si(CH₃)₂—CH₃ (Cl—Si with CH₃, CH₃) | 60° | 119° | >95% | Cl—Si(CH₃)(CH₃)—CH₂—Cl | 94.2% |
| | | | | | Overchlorinated product | 5.4% |
| | | | | | Reactant | 0.4% |
| 5 | CH₃—Si(CH₃)₂—CH₃ | 24° | 104° | >95% | H₃C—Si(CH₃)(CH₃)—CH₂—Cl | 91.1% |
| | | | | | Overchlorinated product | 8.9% |
| | | | | | Reactant | 0.0% |
| 6 | Cl—Si(Cl)(Cl)—CH₃ | 68° | 125° | >95% | Cl—Si(Cl)(Cl)—CH₂—Cl | 95.9% |
| | | | | | Overchlorinated product | 4.1% |
| | | | | | Reactant | 0.0% |
| 7 | H₃C—C(=O)—CH₃ | 59° | 93° | >95% | H₃C—C(=O)—CH₂—Cl | 95.0% |
| | | | | | Overchlorinated product | 2.0% |
| | | | | | Reactant | 2.0% |

What is claimed is:

1. In a free radical halogenation process for the preparation of product of formula I $$R\text{—}CY \qquad \text{I}$$

wherein
Y is $H_2X$, $HX_2$ or $X_3$;

R is $CH_3\overset{O}{\overset{\|}{C}}$—;

$Si(Cl)_m(CH_3)_n$, wherein m is 0 to 3, n is 0 to 3, and m+n is 3; phenyl; or phenyl substituted with Cl, Br, F, $OR^1$, $SR^1$ or $NO_2$;
$R^1$ is $C_1$-$C_3$ alkyl; and
X is Cl or Br;
by reacting starting material of the formula R—$CH_3$ and $X_2$ wherein R and X are as defined for formula I; the improvement comprising:
vaporizing starting material into a reaction zone beneath a condenser zone and above a separation zone affixed to a pot containing liquid product; and
conducting the reaction in said reaction zone with said separation zone continuously and selectively separating at least one product compound of Formula $RCH_2X$, $RCHX_2$ or $RCX_3$ from the reaction zone.

2. The process of claim 1 wherein the product compound is $RCH_2X$.

3. The process of claim 1 wherein the reaction is conducted without recycle of the reactants.

4. The process of claim 1 wherein the $X_2$ is introduced into the reaction zone.

5. The process of claim 1 wherein the ratio of R—$CH_3$ to $X_2$ in the reaction zone is maintained at greater than or equal to 4/1.

6. The process of claim 1 wherein the temperature of the reaction zone is maintained as less than or equal to 6° C. higher than the boiling point of the reactant R—$CH_3$.

7. The process of claim 1 wherein R is $Si(Cl_2)CH_3$ and $X_2$ is chlorine.

8. The process of claim 1 wherein the top portion of the separation column serves as the reaction zone.

9. The process of claim 1 conducted in a continuous mode wherein the product of Formula I is withdrawn from the reaction pot and $RCH_3$ is fed in at a rate to maintain constant volume in the pot.

10. The process of claim 1, wherein the reaction zone is located in a distillation column.

11. A free radical halogenation process for the preparation of a product compound of the formula R—CY by reacting a starting material of the formula R—$CH_3$ with $X_2$, wherein Y is selected from the group consisting of $H_2X$, $HX_2$ and $X_3$; X is selected from the group consisting of Cl and Br; R is selected from the group consisting of (i) phenyl, (ii) phenyl substituted with Cl, Br, F, $OR^1$, $SR^1$ or $NO_2$, (iii)

$CH_3\overset{O}{\overset{\|}{C}}$— and (iv) $Si(Cl)_m(CH_3)_n$, wherein m is 0 to 3, n is 0 to 3, and m+n is 3; and $R^1$ is $C_1$-$C_3$ alkyl; characterized by:
(a) adding vapor phase starting material from a separation zone to a reaction zone located beneath a condenser zone, said separation zone being below the reaction zone and being affixed to a pot containing liquid product;
(b) feeding $X_2$ above the liquid level in the pot; and (c) conducting the reaction in said reaction zone with said separation zone continuously and selectively separating the product compound from the reaction zone.

12. The process of claim 11, wherein the separation zone is a distillation column; and wherein $X_2$ is fed at the top of the distillation column.

13. The process of claim 11, wherein $X_2$ is fed below the reaction zone, mixes with rising vapor and enters the reaction zone.

14. The process of claim 13, wherein the reaction zone is subjected to light as an energy source for free radical formation.

15. The process of claim 11, wherein the reaction zone is at the top part of a separation column which has a lower part wherein reactant and product are separated.

16. The process of claim 15, wherein the surface area of the reaction zone is designed to hold up liquid which enters the reaction zone from the top after condensing at the condenser zone.

17. A free radical halogenation process for the preparation of a product compound of the formula R—CY by reacting a starting material of the formula R—CH$_3$ with $X_2$, wherein Y is selected from the group consisting of $H_2X$, $HX_2$ and $X_3$; X is selected from the group consisting of Cl and Br; R is selected from the group consisting of (i) phenyl, (ii) phenyl substituted with Cl, Br, F, OR$^1$, SR$^1$ or NO$_2$, (iii) 
and (iv) Si(Cl)$_m$(CH$_3$)$_n$, wherein m is 0 to 3, n is 0 to 3, and m+n is 3; and R$^1$ is C$_1$-C$_3$ alkyl; characterized by:
(a) adding vapor phase starting material to a reaction zone located beneath a condenser zone, by vaporizing starting material from a pot containing liquid starting material through a separation zone affixed to said pot below the reaction zone; and adding liquid phase starting material to the reaction zone by condensing in said condenser zone starting material which passes from the reaction zone to the condenser zone, and returning condensed starting material to the reaction zone;
(b) feeding $X_2$ above the liquid level in the pot; and
(c) conducting the reaction in said reaction zone with said separation zone continuously and selectively separating the product compound from the reaction zone.

18. The process of claim 17, wherein $X_2$ is fed below the reaction zone, mixes with rising vapor and enters the reaction zone.

19. The process of claim 17, wherein the reaction zone is at the top part of a separation column which has a lower part wherein reactant and product are separated.

20. The process of claim 19, wherein the reaction zone is packed with glass beads to hold up liquid which enters the reaction zone from the top after condensing in the condenser zone.

* * * * *